(12) United States Patent
Levenson et al.

(10) Patent No.: US 7,666,589 B2
(45) Date of Patent: Feb. 23, 2010

(54) METHYLATION PROFILE OF BREAST CANCER

(75) Inventors: Victor V. Levenson, Chicago, IL (US); Ronald B. Gartenhaus, Northbrook, IL (US)

(73) Assignee: Northwestern University, Evanston, IL (US)

( * ) Notice: Subject to any disclaimer, the term of this patent is extended or adjusted under 35 U.S.C. 154(b) by 81 days.

(21) Appl. No.: 10/677,701

(22) Filed: Oct. 2, 2003

(65) Prior Publication Data

US 2004/0137474 A1 Jul. 15, 2004

Related U.S. Application Data

(60) Provisional application No. 60/415,628, filed on Oct. 2, 2002.

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search ................. None
See application file for complete search history.

(56) References Cited

U.S. PATENT DOCUMENTS 6,605,432 B1 * 8/2003 Huang ................... 435/6

OTHER PUBLICATIONS

Yan et al. (Clinical Cancer Research, vol. 6, pp. 1432-1438, Apr. 2000).*
Ferguson et al. (Current Genomics, vol. 1, pp. 41-58, 2000).*
Herman et al. (Cancer Research, vol. 56, pp. 722-727, Feb. 1996).*
Bovenzi et al (Anti-Cancer Drugs, vol. 10, pp. 471-476, 1999).*
Du et al. (Cancer Research, vol. 61, pp. 8094-8099, Nov. 2001).*
Paz et al (Cancer Research, vol. 62, pp. 4519-4524, Aug. 2002).*
Worm et al. (J. of Biological Chemistry, vol. 276, No. 43, pp. 39990-40000, Aug. 2001).*
Kusui et al. "DNA Methylation of the human oxytocin receptor gene promoter regulates tissue-specific gene suppression" Biochemical and Biophysical Research Communications. vol. 289, pp. 681-686, 2001.*
Maat et al. (Investigative Ophthalmology, Visual Science, vol. 48, No. 2, pp. 486-490, Feb. 2007).*
Henrique et al. (Clin Cancer Research, vol. 13, No. 20, pp. 6122-6129, Oct. 2007).*
Suzuki et al. (Cancer Letters, vol. 242, pp. 222-230, 2006).*
Chang et al. (J. Mol. Med, vol. 83, pp. 132-139, 2005).*
Maruya et al. (Clinical Cancer Research, vol. 10, pp. 3825-3830, Jun. 2004).*
House (J. Gastrointest Surg, vol. 7, pp. 1004-1014, 2003).*
Wong (Cancer Research, vol. 39, pp. 71-73, 1999).*
Broude et al. (PNAS, vol. 98, No. 1, pp. 206-211, Jan. 2001).*
Pogribny et al. (Biochemical and Biophysical Research Communications, vol. 262, pp. 624-628, 1999).*
Yang et al (Gynecologic Oncology, vol. 93, pp. 435-440, 2004).*
Miyamoto et al. (Jpn, J. Clin, Oncol, vol. 35, No. 6, pp. 293-301, 2005).*
Cooper et al., DNA 2:131 [1983].
Baylin et al., AIDS Res Hum Retroviruses 8:811 [1992].
Rountree et al., Oncogene. 20: 3156 [2001.
Jones, Cancer Res. 46:461 [1986].
Villar-Garea and Esteller, Current Drug Metabolism, 4:11 [2003].
Lin et al. Cancer Research 61:8611 [2001].
Young and Smith J. Biol. Chem. 276:19610 [2001]).
Herman et al., PNAS 93:9821 [1996].
Yang et al., Cancer Res. 61:7025 [2001].
Taylor et al., Leukemia 2001, 15:583-589.
Issa et al., Cancer Res. 57:1678 [1997].
Yang et al., Endocr Relat Cancer. 8: 115-127 [2001]).
Singer-Sam et al., "A quantitative HpaII-PCR assay to measure methylation of DNA from a small number of cells," Nucleic Acids Res. Feb. 11, 1990;18(3):687.
Singer-Sam et al., "Use of a HpaII-polymerase chain reaction assay to study DNA methylation in the Pgk-1 CpG island of mouse embryos at the time of X-chromosome inactivation," Mol Cell Biol. Sep. 1990;10(9):4987-9.
Silva, JM et al; Aberrant DNA methylation of the p16INK4a gene in plasma DNA of breast cancer patients; British Journal of Cancer, 1999, vol. 80, No. 8, pp. 1262-1264.
Silva, Jose M. et al; Presence of Tumor DNA in Plasma of Breast Cancer Patients: Clinicopathological Correlations; Cancer Research, Jul. 1, 1999, vol. 59, pp. 3251-3256.
Silva, Jose M. et al; Persistance of Tumor DNA in Plasma of Breast Cancer patients After Mastectomy; Annals of Surgical Oncology, 2002, vol. 9, No. 1, pp. 71-76.
UniProtKB/Swiss-Prot entry P53355; Available as of Oct. 31, 2008.
UniProtKB/TrEMBL entry Q9UET8; Available as of Oct. 31, 2008.
UniProtKB/Swiss-Prot entry Q9ULC4; Available as of Oct. 31, 2008.
UniProtKB/Swiss-Prot entry P42771; Available as of Oct. 31, 2008.
UniProtKB/Swiss-Prot entry Q02548; Available as of Oct. 31, 2008.
UniProtKB/Swiss-Prot entry P07996; Available as of Oct. 31, 2008.
UniProtKB/Swiss-Prot entry O14788; Available as of Oct. 31, 2008.
UniProtKB/Swiss-Prot entry P40337; Available as of Oct. 31, 2008.
Sharma, Gayatri et al, "Promoter Hypermethylation of p16INK4A, p14ARF, CyclinD2 and Slit2 in Serum and Tumor DNA from Breast Cancer Patients", Science Direct, Life Sciences 80 (2007) 1873-1881.
Tan, Sing-Huang et al, "Detection of Promoter Hypermethylation in Serum Samples of Cancer Patients by Methylation-Specific Polymerase Chain Reaction for Tumour Suppressor Genes Including RUNX3", Oncology Reports 18: 1225-1230, 2007.

* cited by examiner

*Primary Examiner*—Jeanine A Goldberg
(74) *Attorney, Agent, or Firm*—Andrus, Sceales, Starke & Sawall, LLP

(57) ABSTRACT

The present invention relates to compositions and methods for cancer diagnostics, including but not limited to, cancer markers. In particular, the present invention provides methods of identifying methylation patterns in genes associated with specific cancers.

7 Claims, 8 Drawing Sheets

Figure 2

| | | T1 | N1 | T2 | N2 | T3 | N3 | T4 | N4 | T5 | N5 | T6 | N6 |
|---|---|---|---|---|---|---|---|---|---|---|---|---|---|
| 217 | p27 | UM | UM | M | M | UM | UM | M | M | M | M | M | M |
| 445 | 14-3-3 | UM | UM | | | M | M | M | M | M | M | | |
| 154 | Apaf2 | | | | | M | M | M | M | | | M | M |
| 268 | BRCA1 | UM | M | M | UM | M | M | M | M | M | M | M | M |
| 584 | Calc | M | M | | | M | M | D | M | UM | D | | |
| 443 | Casp8 | M | UM | | | UM | M | UM | M | M | M | | |
| 242 | CycD2 | M | M | | | M | M | M | M | M | M | M | UM |
| 367 | DAPK | UM | M | | | M | M | M | M | M | M | M | M |
| 659 | E-cadr | UM | M | | | M | M | UM? | UM? | M | M | | |
| 552 | EDNRB | UM | UM | | | UM | M | M | M | M | M | M | M |
| 586 | EP300 | M | M | | | | | M | M | | | | |
| 465 | ERa-proximal | UM | UM | M | M | M | M | M | M | M | M | M | M |
| 508 | ERa-distal | M | M | | | M | M | M | M | M | M | M | M |
| 523 | Fas | UM | UM | | | UM | M | M | UM | M | D? | M | M |
| 306 | FHIT | M | M | | | UM | UM | M | UM | M | UM | | |
| 286 | GPC3 | M | M | | | M | M | M | M | M | M | M | M |
| 288 | GR | M | M | | | UM | M | M | M | M | M | M | M |
| 366 | GSTP1 | UM | UM | M | M | M | M | M | M | M | M | M | M |
| 495 | HIC1 | M | M | | | M | M | M | M | M | M | M | M |
| 400 | HIN | M | UM | UM | UM | M | M | M | M | M | M | M | M |
| 418 | hMLH1 | | | | | M | UM | M | M | UM | UM | UM | M |
| 237 | hMSH2 | | | | | M | M | M | M | | | M | M |
| 350 | ICAM1 | UM | UM | | | M | M | M | M | M | M | M | M |
| 704 | MCJ | UM | M | | | UM | UM | UM | | | | | |
| 440 | MCT-1 | D | M | | | UM | UM | M | M | M | M | | |
| 650 | MDGI | M | UM | | | UM | UM | UM | UM | D | D | | |
| 306 | MDR-1 | M | M | | | M | UM | M | UM | M | M | M | |
| 190 | MGMT | | | | | M | M | M | M | | | M | M |
| 540 | Muc2 | UM | M | M | M | M | M | M | M | M | M | M | M |
| 716 | Myf | M | M | | | M | M | UM | UM | M | M | UM | UM |
| 380 | p15 | M | M | | | D | UM | UM | UM | D | D | UM | D |
| 229 | p16 | UM | UM | | | UM | M | D | D | D | D | D | D |
| 249 | p21 | UM | M | | | M | M | UM | UM | M | M | M | UM |
| 471 | p57 | UM | M | | | UM | M | M | UM | M | | UM | M |
| 337 | p73 | M | M | | | UM | M | M | UM | M | M | UM | M |
| 175 | Pax5 | M | M | | | M | M | M | M | M | M | M | M |
| 315 | PR-1proximal | | | | | M | M | UM | M | UM | UM | M | M |
| 485 | PR-2distal | M | M | | | M | M | M | M | M | M | | |
| 467 | RARb2 | | | | | M | M | M | M | | | | |
| 329 | Rassf1A | M | M | M | M | M | M | M | M | M | M | M | M |
| 359 | RB1 | M | M | | | M | M | M | M | M | M | M | M |
| 453 | RFC1 | M | M | | | M | M | UM | M | M | UM | M | M |
| 234 | RIZ1 | M | M | | | M | M | M | M | M | M | M | M |
| 493 | S100A2 | M | M | | | M | UM | D | M | D | M | | |
| 357 | SOCS1 | M | UM | | | M | M | M | M | M | M | M | M |
| 395 | SRBC | M | M | | | M | M | M | M | M | M | UM | M |
| 196 | SYK | M | M | | | M | M | M | M | M | M | M | M |
| 290 | TBSP* | M | UM | | | UM | M | M | UM | UM | UM? | M | UM |
| 200 | TES** | M | M | | | M | UM | M | UM | M | M | M | M |
| 355 | TMS1 | M | M | | | M | M | M | M | M | M | M | M |
| 384 | TRANCE | M | M | | | M | M | M | M | M | M | M | M |
| 633 | uPA | | | | | | | | | | | UM | M? |
| 146 | VHL | M | M | | | M | M | M | M | M | M | M | M |

Figure 2 continued

| | |
|---|---|
| 217 | |
| 445 | Negative regulator of breast cancer growth |
| 154 | |
| 268 | Silencing = increased risk of BC; no meth in normal; meth in diff path |
| 584 | |
| 443 | Correlates with Rassf1a meth in neuroblastoma |
| 242 | Methylation frequent in BC (25%), correlates with higher grade, different in intraductal and invasive |
| 367 | Methylation correlates with invasive lobular carcinoma, no p53 overexpression, ER positivity |
| 659 | Loss of expression correlates with poor survival and ER status; expressed in inflammatory BC. |
| 552 | Potential role in osteoblastic mets |
| 586 | histone acetyltransferase |
| 465 | Silencing - poor risk factor |
| 508 | Silencing - poor risk factor |
| 523 | Reduced expression - lower DFS, resistance to Tam; expr in 50% of BC vs 91% of benign lesions |
| 306 | Progressive loss in breast cancer |
| 286 | Growth inhibitor; lost in breast cancer |
| 288 | Expression is higher in higher grade |
| 366 | |
| 495 | Expression - good prognostic marker |
| 400 | Expressed only in normal but not in breast cancer |
| 418 | Repair gene |
| 237 | Repair gene |
| 350 | Expression inhibits growth of breast cancer |
| 704 | Repair gene |
| 440 | Novel oncogene |
| 650 | Silencing increases chance of tumor growth |
| 306 | |
| 190 | Low expression equals poor survival |
| 540 | Expression - less aggressive behavior, lymph node mets, higher grade of DCIS |
| 716 | Hypermethylation in higher grade tumors |
| 380 | Frequently deleted in cancer |
| 229 | Frequently deleted in cancer |
| 249 | Expression - in higher grade; no correlation with prognosis |
| 471 | Loss - poor prognosis. Maternally expressed; expression - better survival at chemotherapy |
| 337 | Overexpression -poor prognosis, higher grade;Reduced expresion - tumorigenesis; in mets |
| 175 | Inhibition leads to loss of growth control via CD19 |
| 315 | Expression predicts response to horm therapy |
| 485 | Expression predicts response to horm therapy |
| 467 | Inhibited in tumors |
| 329 | Methylated in breast tumors (43%) and small-cell lung cancer (100%) |
| 359 | Loss of expression predicts faster growth of tumor; correlates with no node mets |
| 453 | Expression - correlates with resistance to folates |
| 234 | Loss of expression - a condition for tumor growth |
| 493 | Expression is lost in cancer |
| 357 | Inhibitor of Jak/Stat; Jak/Stat regulates differention; silencing - very freq in AML; no correlation with outcome |
| 395 | Interacts with BRCA-1; methylated in cancer cell lines |
| 196 | Reduced expression correlates with metastasis |
| 290 | Expression of TBSP - good prognosis in DCIS; reduced metastasis |
| 200 | Putative tumor-suppressor, freq methylated |
| 355 | Reduced expression correlates with tumor growth and resistance to apoptosis |
| 384 | Expression in bone mets, unclear whether in breast cancer cells or not |
| 633 | Increased activity correlates with mets |
| 146 | Deletions of chromosamal region in breast cancer |

Figure 3

| Gene | 14-3-3 sigma | Apaf2 | BRCA-1 | Calcitonin | Caspase 8 | CycD2 | DAPK | E-cadherin | EDNRB | Ep300 | ERa-B | ERa-A | Fas | FH IT | GPC3 |
|---|---|---|---|---|---|---|---|---|---|---|---|---|---|---|---|
| MDA | M | M | UM | M | UM | M | UM | M | M | UM | M | M | UM | UM | M |
| MCF-7 | M | M | UM | UM | UM | M | M | M | M | UM | M | UM | UM | UM | M |
| T47D | M | UM | UM | UM | M | M | UM | M | M | M | M | UM | UM | UM | UM |
| T1 | UM | M | UM | M | M | M | UM | ND | UM | M | M | UM | UM | M | M |
| N1 | UM | M | M | UM | UM | M | M | ND | UM | M | M | UM | UM | M | M |

| Gene | GR | GSTP1 | HIC1 | HIN | hMLH1 | ICAM1 | MCT1 | MDGI | MDR1 | MGMT | MCJ | Muc2 | Myf | p15 INK4B | p16 INK4A | p21 waf1 | p27 Kip1 | p57 Kip2 | p73 | PAX | PR | RassHa | RB-1 | RFC-1 | RIZ | S100 A2 | SOCS-1 |
|---|---|---|---|---|---|---|---|---|---|---|---|---|---|---|---|---|---|---|---|---|---|---|---|---|---|---|---|
| MDA | UM | M | M | M | M | M | M | M | M | UM | M | M | M | D | D | UM | UM | UM | UM | M | M | M | UM | M | M | M | UM |
| MCF-7 | UM | M | M | M | UM | M | UM | M | M | UM | UM | M | M | D | D | UM | UM | UM | UM | M | M | M | UM | UM | UM | M | UM |
| T47D | M | M | M | M | UM | UM | ND | M | M | UM | UM | M | UM | D | D | UM | UM | M | M | M | M | M | M | UM | M | M | UM |
| T1 | M | UM | M | M | ND | UM | ND | M | M | UM | UM | M | M | UM | M | M | UM | M | M | M | M | M | M | M | M | M | M |
| N1 | M | UM | M | UM | ND | UM | ND | UM | M | ND | M | M | M | UM | UM | M | UM | M | M | M | M | M | M | M | M | M | UM |

| Gene | SRBC | SYK | TES | THBS | TMS1 | TRANCE | uPA | VHL |
|---|---|---|---|---|---|---|---|---|
| MDA | UM | M | UM | UM | M | M | UM | UM |
| MCF-7 | M | M | M | UM | M | M | UM | UM |
| T47D | M | UM | M | UM | M | UM | M | M |
| T1 | M | M | M | M | M | M | ND | M |
| N1 | M | M | M | M | M | M | ND | M |

Figure 4
A. Northern blot
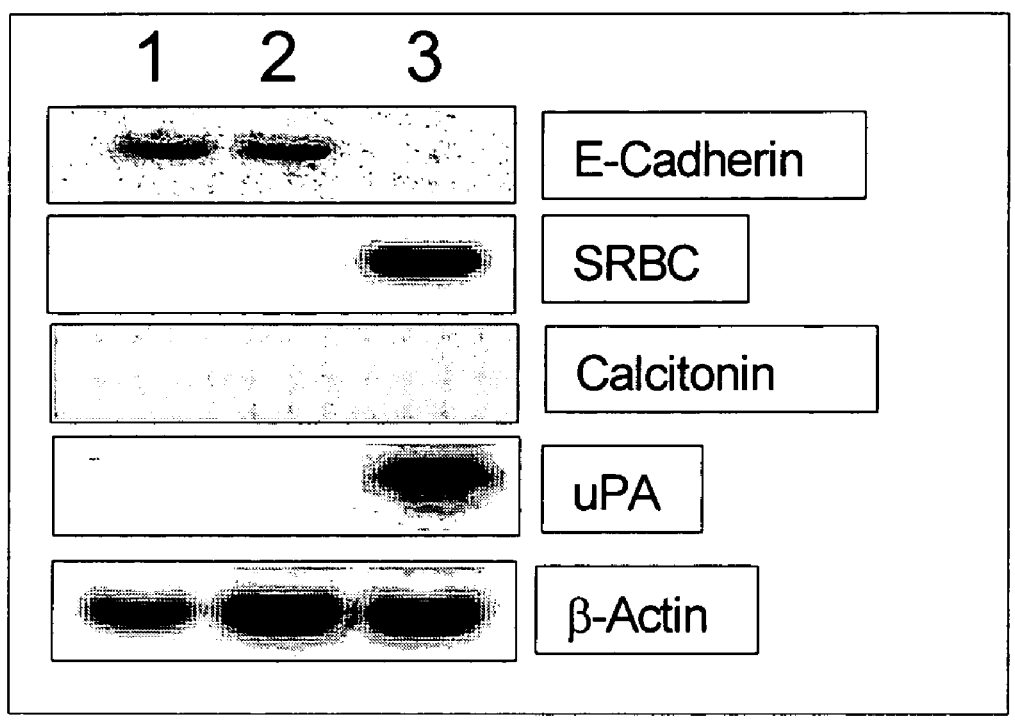
B. Methylation-specific PCR
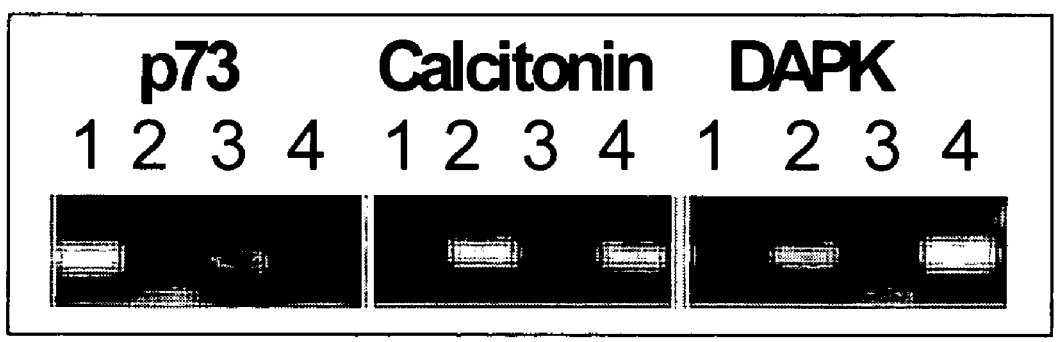

Figure 6

| CTCL (n=6-8) | BRCA1 | SYK | RIZ | p15 | MCT-1 | cycD2 | Rb1 | 14-3-3σ |
|---|---|---|---|---|---|---|---|---|
| | 100% | 14% | 12% | 0% | 16% | 0% | 0% | 100% |

| | Control Samples (n=8) | Summary of T-cell lines (n=6) | HUT 78 | HUT 102 | C91PL | EC155 | N1185 | N1186 |
|---|---|---|---|---|---|---|---|---|
| BRCA1 | 0% | 50% | M | U | M | M | U | U |
| SYK | 0% | 16% | M | U | U | U | U | U |
| RIZ | 0% | 0% | U | U | U | U | U | U |
| p15$^{ink4a}$ | 12% | 40% | ? | U | M | M | U | U |
| p16$^{ink4B}$ | 0% | 0% | ? | U | U | U | U | U |
| MCT-1 | 0% | 0% | U | U | U | M | U | U |
| MYF | 0% | 50% | M | U | M | M | U | U |
| calcitonin | 0% | 33% | M | U | U | M | U | U |
| p57$^{kip2}$ | 0% | 0% | U | ? | U | ? | U | U |
| CD79b | 0% | 33% | M | U | U | M | U | U |
| p27$^{kip1}$ | 0% | 0% | U | U | U | U | U | U |
| RAR | 0% | 0% | U | U | U | U | U | U |
| cycD2 | 12% | 0% | U | U | U | U | U | U |
| Rb1 | 0% | 16% | U | U | U | M | U | U |
| HIN | 0% | 0% | U | U | U | U | U | U |
| HIC1 | 0% | 50% | M | U | M | M | U | U |
| p73 | 0% | 16% | M | U | U | M | U | U |
| RASSF1A | 0% | 16% | M | U | U | U | U | U |
| 14-3-3σ | 100% | 83% | M | U | M | M | M | M |
| DAPK | 0% | 33% | M | U | U | U | M | U |
| SRBC | ? | 33% | M | U | U | U | M | M |
| Rab | 0% | 16% | M | U | U | U | U | U |
| ERα | 0% | 66% | M | U | M | M | U | M |
| PR | 0% | 50% | M | U | M | M | U | U |
| GSTP | 0% | 16% | U | U | U | U | U | U |
| MGMT | 0% | 0% | U | U | U | U | U | U |
| MDR1 | 0% | 16% | M | U | U | U | U | U |
| hMLH | 0% | 0% | U | U | U | U | U | U |
| p21$^{waf1}$ | 0% | 0% | U | U | U | U | U | U |

Figure 7

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tcgcccttcc caacagttgc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cgcgtttcgg tgatgacggt                                          20
```

METHYLATION PROFILE OF BREAST CANCER

This application claims priority to provisional patent application Ser. No. 60/415,628, filed Oct. 2, 2002, which is herein incorporated by reference in its entirety.

This application was funded in part by grant number R21 CA097511 awarded by the National Cancer Institute. The government may have certain rights in the invention.

FIELD OF THE INVENTION

The present invention relates to compositions and methods for cancer diagnostics, including but not limited to, cancer markers. In particular, the present invention provides methods of identifying methylation patterns in genes associated with specific cancers.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of Estrogen Receptor (ER) and Progesterone Receptor (PR) levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more treatments are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. They may be used separately or, most often, in different combinations.

Several diagnostic tests are used to rule out or confirm cancer. For many cancers, the most definitive way to do this is to take a small sample of the suspect tissue and look at it under a microscope—this process is called a biopsy. However, many biopsies are invasive, unpleasant procedures with their own associated risks, such as pain, bleeding, infection, and tissue or organ damage. In addition, if a biopsy does not result in an accurate or large enough sample, a false negative or misdiagnosis can result, often required that the biopsy be repeated. What is needed in the art are improved methods to specifically detect, characterize, and monitor specific types of cancer.

SUMMARY OF THE INVENTION

The present invention relates to compositions and methods for cancer diagnostics, including but not limited to, cancer markers. In particular, the present invention provides methods of identifying methylation patterns in genes associated with specific cancers.

Accordingly, in some embodiments, the present invention provides a method, comprising providing a biological sample from a subject, the biological sample comprising genomic DNA; detecting the presence or absence of DNA methylation in one or more genes to generate a methylation profile for the subject; and comparing the methylation profile to one or more standard methylation profiles, wherein the standard methylation profiles are selected from the group consisting of methylation profiles of non cancerous samples and methylation profiles of cancerous samples. In certain embodiments, the detecting the presence or absence of DNA methylation comprises the digestion of the genomic DNA with a methylation-sensitive restriction enzyme followed by multiplexed amplification of gene-specific DNA fragments with CpG islands.

In further embodiments, the present invention provides a method of characterizing cancer, comprising providing a biological sample from a subject diagnosed with cancer, the biological sample comprising genomic DNA; and detecting the presence or absence of DNA methylation in DAPK, GSTP, p15, MDR1, PR, Calcitonin, RIZ, and RARbeta genes, thereby characterizing cancer in the subject. In some embodiments, the method further comprises the step of detecting the presence or absence of DNA methylation in one or more genes selected from the group consisting of S100, SRBC, BRCARalGDS, HIN1, Sy, Cyclin D2, TMS1, HIC-1, hMLH1, Rab6c, E-cadherin, 14-3-3sigma, and MDGI. In some embodiments, the characterization of cancer comprises detecting the presence or absence of chemotherapy resistant cancer. In some embodiments, the chemotherapy is selected from the group consisting of tamoxifen and raloxifene. In some embodiments, the chemotherapy is a nonsteroidal selective estrogen receptor modulator.

In other embodiments, the characterization of cancer comprises determining a chance of disease-free survival. In still further embodiments, the characterization of cancer comprises determining the risk of developing metastatic disease. In yet other embodiments, the characterization of cancer comprises monitoring disease progression in said subject. In some embodiments, the biological sample is a biopsy sample. In other embodiments, the biological sample is a blood sample. In some embodiments, the DNA methylation comprises CpG methylation. In some preferred embodiments, detecting the presence or absence of DNA methylation comprises the digestion of said genomic DNA with a methylation-sensitive restriction enzyme followed by multiplexed amplification of gene-specific DNA fragments with CpG islands. In some embodiments, the methylation-sensitive restriction enzyme comprises Hin 6I. In other embodiments the methylation sensitive restriction enzyme comprises HpaII. In certain embodiments, the cancer is breast cancer. In other embodiments, the cancer is lymphoma.

The present invention further provides a method of diagnosing cancer, comprising providing a biological sample from a subject, the biological sample comprising genomic DNA; and detecting the presence or absence of DNA methylation in DAPK, GSTP, p15, MDR1, Progesterone Receptor, Calcitonin, RIZ, and RARbeta genes, thereby diagnosing cancer in the subject. In some embodiments, the method further comprises the step of detecting the presence or absence of DNA methylation in one or more genes selected from the group consisting of S100, SRBC, BRCA, RalGDS, HIN1, Sy, Cyclin D2, TMS1, HIC-1, hMLH1, Rab6c, E-cadherin, 14-3-3sigma, and MDGI. In some embodiments, the subject is at high risk of developing cancer. In some embodiments, the cancer is breast cancer. In some embodiments, the biological sample is a blood sample. In some embodiments, the DNA methylation comprises CpG methylation. In some embodiments, detecting the presence or absence of DNA methylation comprises the digestion of the genomic DNA with a methylation-sensitive restriction enzyme followed by multiplexed amplification of gene-specific DNA fragments with CpG islands. In some embodiments, the methylation-sensitive restriction enzyme comprises Hin6I. In other embodiments, the methylation-sensitive restriction enzyme comprises HpaII.

The present invention additionally provides a kit for characterizing cancer, comprising reagents for detecting the presence or absence of DNA methylation in DAPK, GSTP, p15, MDR1, Prostaglandin Receptor, Calcitonin, RIZ, and RARbeta genes. In some embodiments, the kit further comprises reagents for detecting the presence or absence of DNA methylation one or more genes selected from the group consisting of S100, SRBC, BRCA, RalGDS, HIN1, Sy, Cyclin D2, TMS1, HIC-1, HMLH1, Rab6c, E-cadherin, 14-3-3sigma, and MDGI. In some embodiments, the kit further comprises instructions for using the kit for characterizing cancer in the subject. In some embodiments, the instructions comprise instructions required by the United States Food and Drug Administration for use in in vitro diagnostic products. In some embodiments, the reagents comprise reagents for digestion of genomic DNA comprising the one or more genes with a methylation-sensitive restriction enzyme followed by multiplexed amplification of gene-specific DNA fragments with CpG islands. In some embodiments, characterizing cancer comprises detecting the presence or absence of chemotherapy resistant cancer. In some embodiments, the chemotherapy is selected from the group consisting of tamoxifen and raloxifene. In some embodiments, the chemotherapy is a nonsteroidal selective estrogen receptor modulator. In other embodiments, characterizing cancer comprises determining a chance of disease-free survival. In still further embodiments, characterizing cancer comprises determining the risk of developing metastatic disease. In yet other embodiments, characterizing cancer comprises monitoring disease progression in the subject. In some embodiments, the cancer is breast cancer.

In some further embodiments, the present invention provides a method of characterizing or diagnosing cancer, comprising providing a biological sample from a subject suspected of having cancer (e.g., lymphoma) or diagnosed with cancer (e.g., lymphoma), the biological sample comprising genomic DNA; and detecting the presence or absence of DNA methylation in BRCA1, MYF, HIC, ER, 14-3-3σ and p15, thereby characterizing or diagnosing cancer in the subject.

DESCRIPTION OF THE FIGURES

FIG. 2 shows the results of the methylation assay of some embodiments of the present invention applied to breast tumor tissue (T1-T6) and normal breast tissue (N1-N6).

FIG. 3 shows the results of the methylation assay of the present invention applied to breast tumor tissue (T1), normal breast tissue (N1) and breast tumor cell lines MDA, MCF-7 and T47D.

FIG. 4 shows confirmation of the results of the methylation assay of some embodiments of the present invention. FIG. 4A shows the results of Northern blot analysis. FIG. 4B shows the results of Methylation specific PCR.

FIG. 6 shows the results of methylation profiling of CTCL samples.

FIG. 7 shows the results of methylation profiling in lymphoma cell lines.

DEFINITIONS

Figure 1:
FIG. 1 shows amplification products using one embodiment of the method of the present invention.

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "host" refers to any animal (e.g., a mammal), including, but not limited to, humans, non-human primates, rodents, and the like, which is to be the recipient of a particular treatment. Typically, the terms "host" and "patient" are used interchangeably herein in reference to a human subject.

As used herein, the term "subject suspected of having cancer" refers to a subject that presents one or more symptoms indicative of a cancer (e.g., a noticeable lump or mass).

A subject suspected of having cancer may also have on or more risk factors. A subject suspected of having cancer has generally not been tested for cancer. However, a "subject suspected of having cancer" encompasses an individual who has received an initial diagnosis (e.g., a CT scan showing a mass) but for whom the sub-type or stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, genetic predisposition, environmental expose, preexisting non cancer diseases, and lifestyle.

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "sub-type of cancer" refers to different types of cancer that effect the same organ (ductal cancer, lobular cancer, and inflammatory breast cancer are sub-types of breast cancer.

As used herein, the term "providing a prognosis" refers to providing information regarding the impact of the presence of cancer (e.g., as determined by the diagnostic methods of the present invention) on a subject's future health (e.g., expected morbidity or mortality).

As used herein, the term "subject diagnosed with a cancer" refers to a subject having cancerous cells. The cancer may be diagnosed using any suitable method, including but not limited to, the diagnostic methods of the present invention.

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalence determination. Additional information is available at the Internet web page of the U.S. FDA.

As used herein, the term "detecting the presence or absence of DNA methylation" refers to the detection of DNA methylation in the promoter region of one or more genes (e.g., cancer markers of the present invention) of a genomic DNA sample. The detecting may be carried out using any suitable method, including, but not limited to, those disclosed herein.

As used herein, the term "detecting the presence or absence of chemotherapy resistant cancer" refers to detecting a DNA methylation pattern characteristic of a tumor that is likely to be resistant to chemotherapeutic agents (e.g., nonsteroidal selective estrogen receptor modulators (SERMs)).

As used herein, the term "determining a chance of disease-free survival" refers to the determining the likelihood of a subject diagnosed with cancer surviving without the recurrence of cancer (e.g., metastatic cancer). In some embodiments, determining a chance of disease free survival comprises determining the DNA methylation pattern of the subject's genomic DNA.

As used herein, the term "determining the risk of developing metastatic disease" refers to likelihood of a subject diagnosed with cancer developing metastatic cancer. In some embodiments, determining the risk of developing metastatic disease comprises determining the DNA methylation pattern of the subject's genomic DNA.

As used herein, the term "monitoring disease progression in said subject" refers to the monitoring of any aspect of disease progression, including, but not limited to, the spread of cancer, the metastasis of cancer, and the development of a pre-cancerous lesion into cancer. In some embodiments, monitoring disease progression comprises determining the DNA methylation pattern of the subject's genomic DNA.

As used herein, the term "methylation profile" refers to a presentation of methylation status of one or more cancer marker genes in a subject's genomic DNA. In some embodiments, the methylation profile is compared to a standard methylation profile comprising a methylation profile from a known type of sample (e.g., cancerous or non-cancerous samples or samples from different stages of cancer). In some embodiments, methylation profiles are generated using the methods of the present invention. The profile may be presented as a graphical representation (e.g., on paper or on a computer screen), a physical representation (e.g., a gel or array) or a digital representation stored in computer memory.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

As used herein, the term "gene targeting" refers to the alteration of genes through molecular biology techniques. Such gene targeting includes, but is not limited to, generation of mutant genes and knockout genes through recombination. When a gene is altered such that its product is no longer biologically active in a wild-type fashion, the mutation is referred to as a "loss-of-function" mutation. When a gene is altered such that a portion or the entirety of the gene is deleted or replaced, the mutation is referred to as a "knockout" mutation.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses and modified viruses) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl, Acad. Sci. USA 79:6777 [1982]) and the human cytomegalovirus (Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "recombinant protein" or "recombinant polypeptide" as used herein refers to a protein molecule that is expressed from a recombinant DNA molecule.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk⁻ cell lines, the CAD gene, which is used in conjunction with CAD-deficient cells, and the mammalian hypoxanthine-guanine phosphoribosyl transferase (hprt) gene that is used in conjunction with hprt⁻ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

Advances in molecular biology are making an impact on the design and development of new, more efficient drugs, and more precise diagnostic procedures. However, there is still a noticeable gap when a given approach is already well established and widely used for research goals, but its clinical applications remain unrecognized and its usefulness for diagnostic and prognostic purposes remains untested.

Microarray-based expression profiling has emerged as a very powerful approach for broad evaluation of gene expression in various systems. However, this approach has its limitations, and one of the most important is the requirement of a certain minimal amount of mRNA: if it is below a certain level due to low promoter activity, short half-life of mRNA, or small amounts of starting material expression of the gene cannot be unambiguously detected. An additional concern is the stability of RNA, which in many cases is difficult to control (e.g., for surgically removed tissue samples), so that the absence of a signal for a certain gene might reflect artificially introduced degradation rather than genuine decrease in expression.

DNA is a much more stable milieu for analysis, and DNA methylation in regions with increased density of CpG dinucleotides (CpG islands) has been shown to correlate inversely with corresponding gene expression when such CpG islands are located in the promoter and/or the first exon of the gene. A number of techniques have been developed for methylation analysis; arguably the most popular of them— methylation-specific PCR or MSP—takes advantage of the modification of unmethylated cytosines by bisulfite and alkali which results in their conversion to uracils, changing their partners from guanosine to thymidine. This change can be detected by PCR with primers that contain appropriate substitutions. A substantial amount of data on gene-specific methylation has been acquired using MSP.

The present invention improves methylation analysis by providing a technique for high throughput analysis without losses in the sensitivity. The first phase of the assay involves digestion of genomic DNA with methylation-sensitive enzyme (e.g., HpaII or Hin6I), which cuts unmethylated, for example, CCGG sites while leaving even hemi-methylated sites intact. Efficiency of this step determines the discriminating power of the approach, since the next procedure— amplification of the CpG island-containing fragment with primers flanking the methylation specific restriction enzyme site—serves mainly to increase the sensitivity of the assay.

The present invention overcomes many of the problems of mRNA arrays (e.g., stability of RNA and quantitation of expression) by evaluating gene expression by measuring methylation profiles of CpG islands. These regions of unusually high GC content have been described in many genes (Cooper et al., DNA 2:131 [1983]); the cytosine of CpG island can be modified by methyltransferase to produce a methylated derivative—5-methylcytosine (Cooper et al., supra; Baylin et al., AIDS Res Hum Retroviruses 8:811 [1992]). If a methylated cytosine is located in the promoter region of a gene, it is likely to be silenced (Cooper et al., supra). Silencing of various tumor suppressor and growth regulator genes (Rountree et al., Oncogene. 20: 3156 [2001]; Yang et al., Endocr Relat Cancer. 8: 115-127 [2001]) has been linked to cancer development and progression in general and breast cancer in particular (Baylin et al., supra; Jones, Cancer Res. 46:461 [1986]). Accordingly, in some embodiments, present invention provides cancer diagnostics comprising the identification of methylation patterns in cancer (e.g., breast cancer) samples. None of the known genes is methylated in all cases of breast cancer; thus simultaneous analysis of several genes within the same sample increases the clinical value of the assay.

I. Diagnosis and Characterization of Cancer

In some embodiments, the present invention provides methods of correlation methylation patterns with clinical outcomes (e.g., patients at high-risk for developing cancer, disease-free survival, resistance to chemotherapy, and development of metastatic disease). In other embodiments, the present invention provides methods of disease monitoring during treatment and rapid screening of the high-risk population.

Differential methylation of CpG islands provides an alternative way to characterize expression—or more accurately, repression—profiles of cell lines and tissues. Repression of heavily methylated genes is thought to depend on interactions of methylated cytosines with MeCP2, which either interferes with transcriptional complex assembly or prevents its movement.

Experiments conducted during the course of development of the present invention provide a novel methylation assay designed to provide a fast estimate on the methylation status of chosen genes. The assay relies on restriction endonuclease specificity to discriminate between methylated and unmethylated sequences, and on PCR reaction to amplify surviving templates. The present invention is not limited to the use of methylation specific restriction enzymes and PCR. Any method that examines methylation state (e.g., by selective cleavage, modification, etc.) followed by detection, is contemplated by the present invention. The number and specifics of the genes analyzed can be altered based on the choice of primers.

The methods of the present invention are amenable to detection of differences in expression profiles when inadequate quantities of starting material are available. In some embodiments, the method includes extensive digestion of genomic DNA with a methylation-sensitive restriction enzyme (e.g., HpaII or Hin6I), followed by multiplexed amplification of gene-specific DNA fragments with CpG islands. Experiments conducted during the course of development of the present invention (Example 1) demonstrated that 25 ng of genomic DNA (~5000 cells) produce a discernible methylation pattern for 4-5 genes. The method was tested with a panel of 32 cancer marker genes (cell cycle control, drug response, putative and known oncogenes, apoptosis regulators, and hormone receptors) using MCF7 cells and T47D cells. Differential CpG island methylation was detected in promoters of p15 INK4b, DAP kinase, GSTP and PR. In addition, T47D cells that have lost expression of ER alpha exhibited differential methylation in promoters of MDR1, calcitonin, RIZ1 and RAR beta compared to parental cells. RNA transcription of selected genes reflected the methylation status of corresponding promoter.

In other embodiments, the assay of the present invention is suitable for use with 200 pg or less of starting genomic DNA, thus making the assay suitable for clinical applications where small amounts of genomic DNA are available (e.g., preserved tissue samples). The assay of the present invention provides the further advantage of multiplex analysis of greater than one (e.g., greater than 50) genes in one reaction.

II. Antibodies

The present invention provides isolated antibodies. In preferred embodiments, the present invention provides monoclonal antibodies that specifically bind to an isolated polypeptide comprised of at least five amino acid residues of the cancer markers described above. In some embodiments, the antibodies are used to confirm or validate the data obtained from methylation analysis. These antibodies find use in the diagnostic and therapeutic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a cancer marker of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Cancer Therapy

In some embodiments, the present invention provides cancer therapies. In some embodiments, the cancer therapies target genes with altered methylation patterns in breast cancer, and in particular, chemotherapy resistant breast cancers. In other embodiments, therapies are used to return a patient to a normal condition (e.g., by reducing expression of a gene or activity of an associated protein that is shown by the diagnostic method of the present invention to be overexpressed in a cell or tissue).

A. Immunotherapy

The cancer markers identified during the development of the present invention find use in cancer immunotherapy. Such methods are improvements over the non-specific chemotherapeutic cancer therapies currently available. For example, in some embodiments, cancer markers are used to generate therapeutic antibodies. In other embodiments, the cancer markers of the present invention find use in the generation of cancer vaccines.

i. Pharmaceutical Compositions

In some embodiments, the present invention provides pharmaceutical compositions that may comprise all or portions of cancer markers polynucleotide sequences, cancer markers polypeptides, inhibitors or antagonists of cancer markers bioactivity, including antibodies, alone or in combination with at least one other agent, such as a stabilizing compound, and may be administered in any sterile, biocompatible pharmaceutical carrier, including, but not limited to, saline, buffered saline, dextrose, and water. The pharmaceutical compositions find use as therapeutic agents and vaccines for the treatment of cancer.

The methods of the present invention find use in treating cancers as described in greater detail below. Antibodies can be administered to the patient intravenously in a pharmaceutically acceptable carrier such as physiological saline. Standard methods for intracellular delivery of antibodies can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, compositions (e.g., antibodies and vaccines) can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions may be administered alone to individuals suffering from cancer.

Depending on the type of cancer being treated, these pharmaceutical compositions may be formulated and administered systemically or locally. Techniques for formulation and administration may be found in the latest edition of "Remington's Pharmaceutical Sciences" (Mack Publishing Co, Easton, Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of antibody or vaccine may be that amount that decreases the presence of cancerous cells (e.g., shrinks or eliminates a tumor or reduces the number of circulating cancer cells). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For antibodies to cancer markers of the present invention, conditions indicated on the label may include treatment of conditions related to cancer.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts antibody levels.

A therapeutically effective dose refers to that amount of antibody that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See e.g., U.S. Pat. Nos. 4,657,760; 5,206,344; or 5,225,212, all of which are herein incorporated by reference).

In some embodiments, the pharmaceutical compositions of the present invention further include one or more agents useful in the treatment of cancer. For example, in some embodiments, one or more antibodies or vaccines are combined with a chemotherapeutic agent. Chemotherapeutic agents are well known to those of skill in the art. Examples of such chemotherapeutics include alkylating agents, antibiotics, antimetabolitic agents, plant-derived agents, and hormones. Among the suitable alkylating agents are nitrogen mustards, such as cyclophosphamide, aziridines, alkyl alkone sulfonates, nitrosoureas, nonclassic alkylating agents, such as dacarbazine, and platinum compounds, such as carboplatin and cisplatin. Among the suitable antibiotic agents are dactinomycin, bleomycin, mitomycin C, plicamycin, and the anthracyclines, such as doxorubicin (also known as adriamycin) and mitoxantrone. Among the suitable antimetabolic agents are antifols, such as methotrexate, purine analogues, pyrimidine analogues, such as 5-fluorouracil (5-FU) and cytarabine, enzymes, such as the asparaginases, and synthetic agents, such as hydroxyurea. Among the suitable plant-derived agents are vinca alkaloids, such as vincristine and vinblastine, taxanes, epipodophyllotoxins, such as etoposide, and camptothecan. Among suitable hormones are steroids. Currently, the preferred drug is adriamycin. However, other suitable chemotherapeutic agents, including additional agents within the groups of agents identified above, may be readily determined by one of skill in the art depending upon the type of cancer being treated, the condition of the human or veterinary patient, and the like.

Suitable dosages for the selected chemotherapeutic agent are known to those of skill in the art. One of skill in the art can readily adjust the route of administration, the number of doses received, the timing of the doses, and the dosage amount, as needed. Such a dose, which may be readily adjusted depending upon the particular drug or agent selected, may be administered by any suitable route, including but not limited to, those described above. Doses may be repeated as needed.

ii. Antibody Immunotherapy

In some embodiments, the present invention provides therapy for cancer comprising the administration of therapeutic antibodies (See e.g., U.S. Pat. Nos. 6,180,357; and 6,051,230; both of which are herein incorporated by reference).

In some embodiments, the therapeutic antibodies comprise an antibody generated against a cancer marker of the present invention conjugated to a cytotoxic agent. Such antibodies are particularly suited for targeting cancer markers expressed on tumor cells but not normal cells. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents will serve as useful agents for attachment to antibodies or growth factors, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See e.g., Ghose et al., Methods Enzymol., 93:280 [1983]).

For example, in some embodiments the present invention provides immunotoxins targeted to cancer markers of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions and described above. In preferred embodiments, administration of an antibody composition of the present invention results in a measurable decrease in cancer (e.g., decrease or elimination of tumor).

iii. Cancer Vaccines

In some embodiments, the present invention provides cancer vaccines directed against a specific cancer. Cancer vaccines induce a systemic tumor-specific immune response. Such a response is capable of eradicating tumor cells anywhere in the body (e.g., metastatic tumor cells). Methods for generating tumor vaccines are well known in the art (See e.g., U.S. Pat. Nos. 5,994,523; 5,972,334; 5,904,920; 5,674,486; and 6,207,147; each of which is herein incorporated by reference).

In some embodiments, tumor vaccines are administered when cancer is first detected (e.g., concurrently with other therapeutics such as chemotherapy). In other embodiments, cancer vaccines are administered following treatment (e.g., surgical resection or chemotherapy) to prevent relapse or metastases. In yet other embodiments, cancer vaccines are administered prophylactically (e.g., to those at risk of a certain cancer).

In some embodiments, the cancer vaccines of the present invention comprise one or more cancer markers in a pharmaceutical composition (e.g., those described above). In some embodiments, the cancer marker is inactivated prior to administration. In other embodiments, the vaccine further comprises one or more additional therapeutic agents (e.g., cytokines or cytokine expressing cells).

In some embodiments (e.g., the method described in U.S. Pat. No. 5,674,486, herein incorporated by reference), selected cells from a patient, such as fibroblasts, obtained, for example, from a routine skin biopsy, are genetically modified to express one or more cytokines. Alternatively, patient cells that may normally serve as antigen presenting cells in the immune system such as macrophages, monocytes, and lymphocytes may also be genetically modified to express one or more cytokines. The cytokine expressing cells are then mixed with the patient's cancer marker, for example in the form of irradiated tumor cells, or alternatively in the form of purified natural or recombinant cancer marker, and employed in immunizations, for example subcutaneously, to induce systemic anti-tumor immunity.

The vaccines of the present invention may be administered using any suitable method, including but not limited to, those described above. In preferred embodiments, administration of a cancer vaccine of the present invention results in elimination (e.g., decrease or elimination of tumors) or prevention of detectable cancer cells.

B. Antisense Therapies

The present invention is not limited to the therapeutic applications described above. Indeed, any therapeutic application that specifically targets tumor cells expressing the cancer markers of the present invention are contemplated, including but not limited to, antisense therapies.

For example, in some embodiments, the present invention employs compositions comprising oligomeric antisense compounds, particularly oligonucleotides, for use in modulating the function of nucleic acid molecules encoding cancer markers antigens of the present invention, ultimately modulating the amount of cancer marker produced. In some embodiments, the antisense therapies target only a specific methylation form of the cancer marker. This is accomplished by providing antisense compounds that specifically hybridize with one or more nucleic acids encoding cancer markers. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers. In the context of the present invention, "modulation" means either an increase (stimulation) or a decrease (inhibition) in the expression of a gene. For example, expression may be inhibited to potentially prevent tumor proliferation or stimulated to increase a cancer-specific immune response (e.g., as a cancer vaccine).

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a cancer marker of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 [1991]).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_3$)$_2$.

Other preferred modifications include 2'-methoxy (2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree C and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption to generate pharmaceutical compositions as described above.

C. RNAi Therapies

In other embodiments, the present invention employs compositions comprising siRNAs in RNAi control of gene expression. RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g., 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al., Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are effective at lowering the amounts of targeted RNA, and by extension proteins, frequently to undetectable levels. The silencing effect can last several months, and is highly specific, because one nucleotide mismatch between the target RNA and the central region of the siRNA is frequently sufficient to prevent silencing (Brummelkamp et al., Science 2002; 296:550-3; and Holen et al., Nucleic Acids Res. 2002; 30:1757-66, both of which are herein incorporated by reference).

D. Methylation Therapies

In yet other embodiments, drugs that alter DNA methylation (e.g., demethylation drugs) are used to treat cancers that are identified by the methods of the present invention as comprising DNA hypermethylation. Exemplary demethylation drugs include, but are not limited to, those disclosed in Villar-Garea and Esteller (Current Drug Metabolism, 4:11 [2003]), Lin et al. (Cancer Research 61:8611 [2001]) and Young and Smith (J. Biol. Chem. 276:19610 [2001]).

IV. Gene Therapy Using Cancer Markers

The present invention also provides methods and compositions suitable for gene therapy to alter cancer marker expression, production, or function. As described above, the present invention provides human cancer marker genes and provides methods of obtaining cancer marker genes from other species. Thus, the methods described below are generally applicable across many species. In some embodiments, it is contemplated that the gene therapy is performed by providing a subject with a copy of a gene that is found (e.g., using the diagnostic methods of the present invention) to be underexpressed in individuals with cancer (e.g., a tumor suppressor gene). Subjects in need of such therapy are identified by the diagnostic methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Felgner and Ringold, Science 337:387-388 [1989]). Particularly useful lipid compounds and compositions for transfer of nucleic acids are described in WO95/18863 and WO96/17823, and in U.S. Pat. No. 5,459, 127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

V. Drug Screening

The present invention provides methods and compositions for using cancer marker as a target for screening drugs that can alter, for example, expression of a cancer marker (e.g., those identified using the above methods) or methylation status of the cancer marker.

For example, in some embodiments, the methods of the present invention are used to evaluate the effect of drugs that alter DNA methylation status. In some embodiments, the methods of the present invention find use in the screening of candidate methylation drugs for efficacy and dosage. In other embodiments, the methods of the present invention are used to determine the specificity of drugs that effect DNA methylation (e.g., to determine the genes effected by DNA demethylation drugs).

In other embodiments, the methods of the present invention are utilized to screen for lifestyle changes (e.g., dietary changes) that effect DNA methylation of genes. For example, in some embodiments, the effects of dietary changes on DNA methylation of particular genes (e.g., tumor suppressor genes) is monitored using the methods of the present invention. The methods of the present invention can thus be used to determine the efficacy of lifestyle changes in cancer prevention.

In other screening methods, candidate compounds are evaluated for their ability to alter cancer marker signaling by contacting cancer marker genes, binding partners, binding partner-associated proteins, or fragments thereof, with the candidate compound and determining binding of the candidate compound to the cancer marker gene or peptide. The protein or protein fragments is/are immobilized using methods known in the art such as binding a GST-cancer marker fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., $E.\ coli$ XA90) in which the expression of the GST fusion protein can be induced with isopropyl-$\beta$-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate cancer marker physiological effects (e.g., cancer progression).

In another screening method, one of the components of the cancer marker/binding partner signaling system, is immobilized. Polypeptides can be immobilized using methods known in the art, such as adsorption onto a plastic microtiter plate or specific binding of a GST-fusion protein to a polymeric bead containing glutathione. For example, GST-cancer marker is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of cancer marker with the other peptide. A variation of this method allows for the screening of compounds that are capable of disrupting a previously-formed protein/protein complex. For example, in some embodiments a complex comprising cancer marker or a cancer marker fragment bound to another peptide is immobilized as described above and contacted with a candidate compound. The dissolution of the complex by the candidate compound correlates with the ability of the compound to disrupt or inhibit the interaction between cancer marker and the other peptide.

Another technique for drug screening provides high throughput screening for compounds having suitable binding affinity to cancer marker expression or peptides and is described in detail in WO 84/03564, incorporated herein by reference. Briefly, large numbers of different small peptide test compounds are synthesized on a solid substrate, such as plastic pins or some other surface. The peptide test compounds are then reacted with cancer marker peptides and washed. Bound cancer marker peptides are then detected by methods well known in the art.

Another technique uses cancer marker antibodies, generated as discussed above. Such antibodies capable of specifically binding to cancer marker genes or peptides compete with a test compound for binding to cancer marker. In this manner, the antibodies can be used to detect the presence of any peptide that shares one or more antigenic determinants of the cancer marker peptide.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with cancer marker and variants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, the host cells are preferably transfected as described above with vectors encoding cancer marker or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the expression or repression of cancer marker gene expression. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. In some embodiments, the reporter gene construct comprises the 5' regulatory region (e.g., promoters and/or enhancers) of a protein whose expression is controlled by cancer marker in operable association with a reporter gene (See Example 4 and Inohara et al., J. Biol. Chem. 275:27823 [2000] for a description of the luciferase reporter construct pBVIx-Luc). Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention or regulate the expression of cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that alter the expression of a cancer marker of the present invention are particularly useful in the treatment of cancers (e.g., breast cancer).

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker protein or biologically active portion thereof is contacted with a test compound, and the ability of the test compound to the modulate cancer marker's activity or expression is determined. Determining the ability of the test compound to modulate cancer marker activity can be accomplished by monitoring, for example, changes in enzymatic activity. The cell, for example, can be of mammalian origin.

The ability of the test compound to modulate cancer marker binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer marker substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer marker.

In yet another embodiment, a cell-free assay is provided in which a cancer marker gene, protein or biologically active portion thereof is contacted with a test compound and the ability of the test compound to bind to the cancer marker gene, protein or biologically active portion thereof is evaluated. Preferred biologically active portions of the cancer marker proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the cancer marker protein or nucleic acid to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BlAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer marker nucleic acids, proteins, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer marker binding or activity determined using standard techniques. Other techniques for immobilizing either cancer marker protein or a target molecule on matrices include using conjugation of biotin and streptavidin. Biotinylated cancer marker protein or target molecules can be prepared from biotin-NHS (N-hydroxysuccinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer marker protein to its target molecule. Such antibodies can be derivatized to the wells of the plate, and unbound target or cancer marker protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 [1998]; Hageand Tweed J. Chromatogr. Biomed. Sci. Appl 699:499-

525 [1997]). Further, fluorescence energy transfer may also be conveniently utilized, as described herein, to detect binding without further purification of the complex from solution.

The assay can include contacting the cancer marker nucleic acid, protein or biologically active portion thereof with a known compound that binds the cancer marker to form an assay mixture, contacting the assay mixture with a test compound, and determining the ability of the test compound to interact with a cancer marker protein, wherein determining the ability of the test compound to interact with a cancer marker protein includes determining the ability of the test compound to preferentially bind to cancer marker or biologically active portion thereof, or to modulate the activity of a target molecule, as compared to the known compound.

To the extent that cancer marker can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer marker protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer marker ("cancer marker-binding proteins" or "cancer marker-bp") and are involved in cancer marker activity. Such cancer marker-bps can be activators or inhibitors of signals by the cancer marker proteins or targets as, for example, downstream elements of a cancer marker-mediated signaling pathway.

Modulators of cancer marker expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer marker mRNA or protein expression can be determined by methods described herein for detecting cancer marker mRNA or protein.

A modulating agent can be identified using a cell-based or a cell free assay, and the ability of the agent to modulate the activity of a cancer marker protein can be confirmed in vivo, e.g., in an animal such as an animal model for a disease (e.g., an animal with breast cancer).

VI. Transgenic Animals Expressing Exogenous Genes and Variants Thereof

The present invention contemplates the generation of transgenic animals comprising an exogenous cancer marker gene of the present invention or mutants and variants thereof (e.g., truncations). In preferred embodiments, the transgenic animal displays an altered phenotype (e.g., increased presence of cancer or drug resistant cancer) as compared to wild-type animals. Methods for analyzing the presence or absence of such phenotypes include but are not limited to, those disclosed herein. In some preferred embodiments, the transgenic animals further display an increased growth of tumors or increased evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated. In other embodiments, transgenic and control animals are given immunotherapy (e.g., including but not limited to, the methods described above) and the effect on cancer symptoms is assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in Manipulating the Mouse Embryo, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

A. Materials and Methods pUC19 plasmid (New England Biolabs) was methylated in vitro using SssI methylase (New England Biolabs) as recommended by the manufacturer.

Breast cancer cells MCF-7 and MDA-MB-231 were purchased from ATCC and cultured as recommended. Briefly, MCF-7 cells were be propagated in Dulbecco modified Eagle medium (DMEM) supplemented with 2 mM L-glutamine, 1.5 g/L sodium bicarbonate, 4.5 g/L glucose, 0.01 mg/ml bovine insulin, 0.1 mM non-essential amino acids and 1.0 mM sodium pyruvate, 10% fetal bovine serum (FBS), penicillin (100 U/ml) and streptomycin (50 µg/ml). For MDA-MB-231 Leibovitz's L-15 medium with 2 mM L-glutamine, 10% fetal bovine serum (FBS), penicillin (100 U/ml) and streptomycin (50 µg/ml) was used. Cells were grown in flasks in tissue culture incubator at 37° C. in an atmosphere of 6% $CO_2$. Stock cultures were frozen in 95% FBS, 5% dimethylsuloxide in liquid $N_2$. Prior to freezing, cells were checked for mycoplasma contamination using Mycoplasma Detection Kit v.2.0 (ATCC). Once a month all cultured cells were discarded, and a new vial of cells was thawed.

DNA was isolated using either QIAamp (Qiagen, reported minimal input 1000 cells). Restriction enzyme digests were performed to completion. A negative control (CPGENOME Universal Methylated DNA from Intergen), DNA from MCF-7 cells with unmethylated fragment in E-cadherin promoter 75, and a positive control (pUC19 DNA) were included. The control reaction is handled as follows: pUC19 DNA is mixed with the genomic DNA sample. The mixture is then separated into control (incubation without the enzyme) and experimental (incubation with the enzyme) samples. After incubation samples are purified and used for PCR with pUC19-specific primers. If there is no product in the digested sample, and expected product in the undigested sample, both control and experimental samples are processed for gene-specific PCR.

Genomic DNA was digested with 20 U of Hin6I (New England Biolabs) in 50 µL of reaction volume at 37° C. as recommended by manufacturer. Digestion was performed in a thermocycler with heated lid to prevent evaporation. The second half of the reaction was cleaned with QIAEX II Gel Extraction Kit (Qiagen) to remove Hin6I, precipitated with ethanol after addition of linear polyacrylamide carrier to minimize losses (GenElute, Sigma, 5 µg/ml final concentration), washed with 70% ethanol and dissolved in 10 µL $dH_2O$. After appropriate dilution, 100 pg of digested pUC 18 was used as a template for the PCR reaction with pUC18-specific primers, which flank Hin6I sites at positions 600 and 634 (forward primer at 407: 5'-TCGCCCTTCCCAACAGTTGC-3', SEQ ID NO:1); reverse primer at 681: 5'-CGCGTTTCG-GTGATGACGGT-3'; SEQ ID NO:2). An equal amount of undigested pUC18 (from RE-minus control) served as a positive control for PCR amplification. The location of Hin6I sites to analyze within pUC19 molecule was chosen entirely at random and serves as an internal control for complete digestion of the sample.

Four µL of digested material from both samples (MCF-7 cells were used as a template for PCR reactions with E-cadherin-specific primers.

PCR Amplification of Selected CpG-Rich Regions of Chosen Gene.

Nested primer amplification was performed, using a previously described procedure (Melki et al., Leukemia. 13: 877 [1999]; Melki et al., Cancer Res. 59: 3730 [1999]) for HIC-1 and E-cadherin genes; ten-fold serial dilutions of the template (DNA from MCF-7 cells) starting with 600 ng. The final amount of template in this experiment (6 pg) corresponds to one genome equivalent for normal human cells $\{(2.9 \times 10^6 \text{ kb}) \times (2 \text{ chromosomes}) \times (6 \times 10^5 \text{ Da/kb}) \times (1.66 \times 10^{-24} \text{ g/Da})\}$.

Preparation and Quality Control of Fluorescently Labeled Fragment

Fluorescently labeled fragments for microarray experiments were prepared by incorporating N,N,N',N'-tetramethyl-6-carboxylrhodamine-conjugated dUTP (TAMRA-dUTP) during the last PCR amplification reaction. This dye has an excitation maximum at 555 nm, emission maximum at 580 nm, and can be used with both automated sequencers (310 or 377, Applied BioSystems, Inc) and the microarray scanner (ScanArray4000XL, Packard Bioscience).

Microarrays: Preparation and Hybridization

Design and synthesis of the oligonucleotides and printing of the slides was done at MWG Biotech. Two different oligonucleotides (40- to 60-mers) represented each PCR fragment. In addition to the 22 genes identified previously, four different genes are used to control upstream processing and hybridization (microarray controls): ribosomal protein RLP14 (D87735), nuclear gene for mitochondrial protein cytochrome c oxidase subunit IV (NM_001861), glyceraldehyde-3-phosphate dehydrogenase (NM_002046), and transcription complex protein TFIID (NM_003194). Oligonucleotides corresponding to the coding sequence of these genes are included on the array.

Hybridization and processing of TAMRA-labeled PCR fragments was done using hybridization chambers (DieTech) as described (DeRisi et al., Nat. Genet. 14:457 [1996]). Detection and quantification of hybridization signal was done using ScanArray4000XL, available at microarray facility.

Controls for microarray hybridization were two CpG-rich fragments from the microarray control genes amplified from CPGENOME Universal Methylated DNA, while two other fragments from the same cluster were amplified using DNA from MCF-7 cells. Positive controls from CPGENOME Universal Methylated DNA were used for normalization and comparison of signals from other genes.

B. Results

Assay Setup and Evaluation of Results

In order to provide adequate control of the digestion reaction, aliquots of methylated or unmethylated pUC19 DNA were added to each genomic DNA, and two digestion reactions were set up. To control for non-specific degradation identical reactions were incubated without the enzyme, so that four aliquots for each genomic DNA sample were analyzed: digestion in the presence of methylated pUC19 DNA, digestion in the presence of unmethylated pUC19 DNA, and two control aliquots.

After digestion, aliquots of the reaction were used to check the efficiency of digestion by PCR with pUC19-specific primers; if products were detected in control samples and in the Hin6I-digested sample with methylated DNA, while no product was detected in the Hin6I-digested sample with unmethylated DNA, the digestion was considered successful.

Selection of the primers and reaction conditions allowed for the amplification of up to four-five different fragments starting with 25 ng genomic DNA (FIG. 1). Undigested samples provided controls for amplification and for the influence of methylated pUC19 DNA (no effect), while samples treated with Hin6I provided independent evidence on the status of gene-specific CpG islands in each sample.

Primer design parameters allowed for the selection of the number of Hin6I site within each amplified fragment (3-7, with an average of 5). Since the overall assay design required only one unmethylated Hin6I site to destroy corresponding template, it was possible to compare methylation intensity in different regions of the genome.

Differences Between MCF7 and T47D Cell Lines

MCF7 cells and T47D cells overexpressing Erα exhibited differential methylation compared to T47D cell lines. (Table 1).

TABLE 1

| Samples | MCF7 | T47D wt | T47D Erα |
|---|---|---|---|
| DAPK | Yes | No | Yes |
| GSTP | Yes | No | Yes |
| p15 | Yes | Yes | Yes |
| MDR1 | Yes | No | Yes |
| Pg Receptor | No | No | No |
| Calcitonin | No | No | Yes |
| RIZ | Yes | No | Yes |
| RARbeta | Yes | Yes | No | No | Yes |

Example 2

Methylation Detection in MDA-MB-231 Breast Cancer Cell Line Treated with 5-Aza-2'-deoxycytidine Cells and Cell Culture Breast cancer cells MDA-MB-231 contain several heavily methylated promoters, which can be demethylated by treatment with 5-aza-2'-deoxycytidine, presenting a good model for methylation studies. MDA-MB-231 cells are cultured as described above. Treatment of cells with 5-aza-2'-deoxycytidine is done as described (Yang et al., Cancer Res. 61:7025 [2001]). Briefly, cells are treated with 0.3 µM of 5-aza-2'-deoxycytidine for 2.5 days and their DNA is isolated.

Sample Processing for the Assay

Preparation of DNA, RE digestion, fragment labeling, array hybridization and signal detection is done as described above. Specifically, inclusion of pUC19 as a control for RE digestion with PCR amplification of the corresponding fragment is a standard positive control for RE digestion in all samples, while amplification of the undigested pUC18 serves as a negative control. PCR amplification, incorporation of fluorescent label and array hybridization is controlled as described above. These controls are done for all specimens. Optionally, these controls are supplemented by an intermediate control of PCR amplification through fragment detection in polyacrylamide gel as described in section below.

Confirmation of Methylation Data by an Independent Method

To confirm methylation data obtained by the methylation assay described herein with MDA-MB-231 cells, methylation-specific PCR (MSP) analysis is performed using the same DNA and CpG-WIZ™ Amplification Kit (Intergen) for p16INK4A, p15INK4B and E-cadherin as described by the manufacturer. Bisulfite modification of DNA is performed as described (Herman et al., PNAS 93:9821 [1996] using CPGENOME DNA Modification Kit (Intergen);

Modified DNA is also used for genomic sequencing of p16INK4A as described (Herman et al., PNAS 93: 9821 [1996]). This provides a second independent control for M3A assay.

Example 3

Methylation Detection in Clinical Material

Ten samples from patients with established diagnosis are used. The samples are banked, formalin-fixed and paraffin-embedded samples from patients with established diagnosis of breast cancer. Surgery is a standard form of treatment offered to these patients. The excised tissue consists of tumor along with some amount of normal tissue and (axillary)

lymph nodes. These are examined in the pathology department and representative samples are fixed in formalin and routinely processed in paraffin. Glass slides from these paraffin blocks are evaluated to determine the type, grade and stage of the cancer. A board certified pathologist identifies morphologically normal and tumor bearing samples. Tissues from normal areas are processed as syngenic negative controls. Healthy tissues from breast reduction surgery is used as allogenic negative controls; comparison of M3A data for these two controls is performed to identify pre-malignant processes in tissues surrounding cancerous cells.

Preparation of DNA from paraffin-embedded formalin-fixed sections is done by a standard de-paraffination procedure as follows: 10 μm sections are mounted on a glass slide, dried at 60° C. for 30 min; incubated in Xylene for 30 min at room temperature, hydrated through 100%, 70% and 50% ethanol (2 min each) and air dried. DNA from the whole section is isolated as described above. Another section taken from the same block is used to isolate DNA with Ex-WAXTM DNA Extraction Kit (Intergen), and DNA yields compared. Average yields and yield variability from five independent experiments is evaluated, and the optimized procedure is used in subsequent experiments with paraffin-embedded formalin-fixed sections.

Evaluation of the sensitivity and specificity of the methylation assay is done in comparison with the MSP as described above for p16INK4A, p15INK5B and E-cadherin using DNA from the same section of paraffin-embedded tissue block. The detection limit of each procedure is determined by eight serial two-fold dilutions of the starting DNA from 3.2 ng to 25 pg. Relative sensitivity of these procedures is compared by evaluating the product yield after equal total number of PCR cycles (combined for pre-amplification and gene-specific amplification steps). It is expected that the sensitivity of the assay is substantially similar to that of MSP; increasing the number of PCR cycles either for WGA or for gene-specific amplification can accommodate a certain reduction in sensitivity for DNA extracted from paraffin-embedded samples.

Specificity of the assays is compared using fluorescently labeled PCR products as described above. The assay for methylation of each gene is applied to 10-15 samples to assess the sensitivity of the assay to detect methylation in tumors. A sensitivity of 90% is targeted (i.e., 90% of the samples assayed will result in a positive signal for methylation for at least one of the genes). If 10 samples are assayed, then, using exact binomial probabilities, 7 or more positive samples indicates that there is a 93% chance that the sensitivity is at least 90%. If 15 samples are assayed, then 11 or more positive samples indicates that there is a 94% chance that the sensitivity is at least 90%. Statistical evaluation of results will be done in collaboration with Biostatistical Support Group of Robert H. Lurie Comprehensive Cancer Center.

Example 4

High-Throughput Methylation Analysis

This Example describes a high-throughput technique for examination of promoter methylation status. The assay relies on complete digestion with methylation-sensitive restriction enzyme and multiplexed PCR amplification with gene-specific primers.

Genomic DNA, which contains a mixture of methylated and unmethylated was purified from the breast cancer cell lines MDA-MB-231, MCF-7 and T47D. The DNA was digested with a methylation sensitive restriction enzyme, which only digests unmethylated DNA. Multiplex PCR was then performed with gene specific primers. In this step, only methylated DNA is amplified.

A comprehensive methylation profile was completed using a set of over 40 promoters of cancer-related genes (See FIGS. 2 and 3). FIG. 2 shows the results of the methylation status of breast tumor tissue (T1-T6) and normal breast tissue (N1-N6). M refers to the detection of a methylated form of the gene; UM refers to the detection of an unmethylated form of the gene; and D refers to the detection of a deletion in the gene. FIG. 3 shows the results of the methylation status of breast tumor tissue (T1), normal breast tissue (N1) and breast tumor cell lines MDA, MCF-7 and T47D. M refers to the detection of a methylated form of the gene, UM refers to the detection of an unmethylated form of the gene, D refers to the detection of a deletion in the gene, and ND refers to genes and cell lines combinations that were not assayed.

Selected results were confirmed by methylation-specific PCR and Northern blotting (See FIG. 4). FIG. 4A shows the results of Northern blot analysis. Lane 1 is MCF-7 cells, lane 2 is T-47D cells and Lane 3 is MDA-MB-231 cells. FIG. 4B shows the results of Methylation specific PCR. Lanes 1 and 2 are MCF-7 cells, lanes 3 and 4 are T-47D cells. Lanes 1 and 3 shows PCR with methylated DNA specific primers and lanes 2 and 4 show PCR with unmethylated DNA-specific primers.

Besides methylation, the assay can detect deletions as shown for p15Ink4B and p16Ink4A in MDA-MB-231 and MCF-7n (FIG. 3). A comparison of detection of DNA templates from formalin-fixed paraffin embedded tissue and cultured cells showed comparable results.

The assay can be completed within a week starting with miniscule amounts of isolated genomic DNA, thus allowing for routine analysis of promoter methylation from clinical samples. Such screening provides useful information on molecular markers for both diagnosis and prognosis, as well as prediction of response to both chemotherapy and hormonal therapy.

Example 5

Methylation Profile of T-Cell Lymphoma

This study used the high throughput method described in Example 4 to analyze promoter methylation status of multiple tumor suppressor genes in T-cell lymphoma/leukemia cell lines as well as in tumor samples of primary human cutaneous T-cell lymphomas (CTCL). Promoter methylation analysis of thirty different genes in cultured cells and tumor samples was determined, demonstrating a methylation profile specific for this type of cancer.

A. Methods

Cell lines: Hut 78 cell line is derived from human CTCL and is HTLV1 negative, whereas the other five lines studied are human adult T-cell leukemia/lymphoma derived cell lines infected with HTLV-1.pUC19 methylation: SssI methylase (New England Biolabs) as described by the manufacturer; purified using DNA Clean Up and Concentrator Kit (Zymo Research).

Genomic DNA isolation and digestion: DNA was isolated using QIAmp Mini Kit (Qiagen) as described. Five hundred ng of genomic DNA was mixed with 100 pg of either methylated or unmethylated pUC DNA and treated with Hin6I (New England Biolabs) for 48 hr as recommended by the manufacturer. Control samples were incubated without the enzyme. After digestion DNA was purified using DNA Clean Up and Concentrator Kit (Zymo Research).

PCR for quality control. One pg of pUC DNA from digested and control samples was amplified with pUC-specific primers in a 30 ml reaction with 2.5 U of KlenTaq (AB Peptides) using manufacturer-supplied buffer. Amplification was done in PE 9600 (Applied Biosystems).

Multiplexed PCR. Twenty ng of genomic DNA from digested and control samples was similarly amplified with gene-specific primers in a 30 ml reaction with 2.5 U of KlenTaq (AB Peptides) using manufacturer-supplied buffer and touch-down hot-start PCR. Sequences of primers are available upon request. Two microliters of the PCR mix were loaded per each lane of 2% agarose gel.

B. Results

Figure 5:
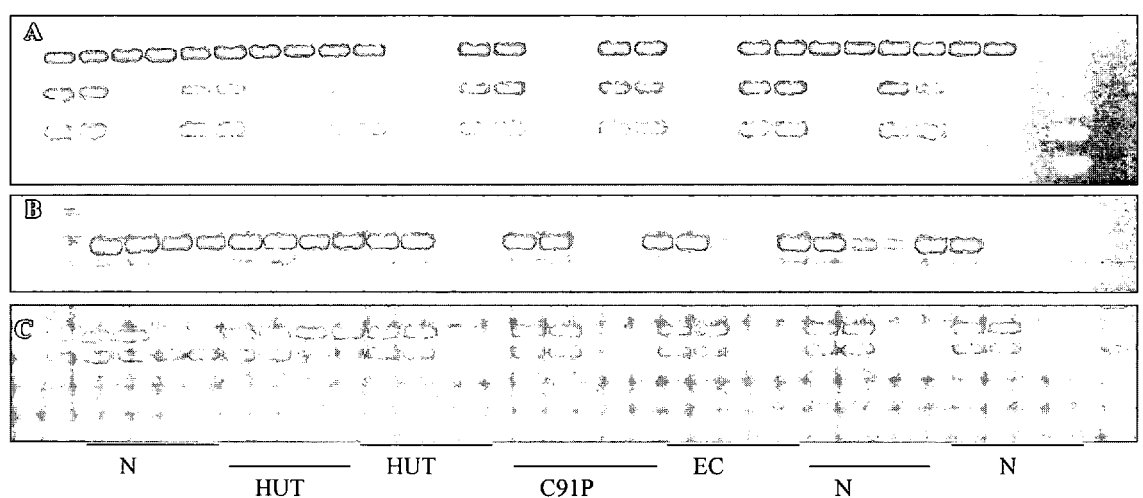
FIG. 5 shows PCR amplification of S100A2; p27Kip1 and Cyclin D2 (panel A); BRCA1 and hMLH1 (panel B); RASSF1A, MCT-1, MGMT, SRBC-1 (panel C).

FIG. 5 shows PCR amplification of S100A2; p27Kip1 and Cyclin D2 (panel A); BRCA1 and hMLH1(panel B); RASSF1A, MCT-1, MGMT, SRBC-1 (panel C) in a mixture of genomic DNA from eight normal donors (N mix) and six different lymphoma cell lines. Each sample is represented by four lanes: two with non-digested template DNA, and two where template DNA was digested with methylation-sensitive restriction enzyme before amplification.

FIG. 6 shows the results of methylation profiling of CTCL samples. FIG. 7 shows the results of methylation profiling of lymphoma cell lines. The results show high frequency of CpG island methylation of BRCA1, MYF, HIC, ER, 14-3-3σ and p15 in T-cell lines studied.

BRCA1 inactivation through methylation was previously shown in sporadic (nonfamilial) breast and ovarian cancer. This is the first report demonstrating hypermethylation of this gene in lymphomas.

Myf is a candidate tumor suppressor gene and is important in control of the cell cycle and lymphomagenesis. Others have shown its hypermethylation in 93% samples of non-Hodgkin lymphomas (NHL) and lymphoid leukemias (Taylor et al., Leukemia 2001, 15:583-589). The results of the present Example extend these findings to include T-cell malignancies.

HIC (hypermethylated in cancer) is a candidate tumor suppressor gene and is known to be a target of p53. It is hypermethylated and silenced in many solid tumors and in 25% of newly diagnosed NHL (Issa et al., Cancer Res. 57:1678 [1997]). The results presented herein suggest that silencing of this TSG is important in T-cell lymphomas as well.

p15Ink4A was not found to be silenced in human CTCL samples studied in the present Example, although 2/6 cell lines showed its methylation. Others have shown its frequent silencing in CTCL often corresponding with disease progression.

14-3-3σ is a potential tumor suppressor gene important for cell cycle control and apoptosis induction. It was frequently methylated in normal lymphocytes, and in T-cell lymphoma cell lines and CTCL.

This is the first report demonstrating that methylation-dependent silencing of BRCA1 can be important for CTCL development. The present invention is not limited to a particular mechanism. Indeed, an understanding of the mechanism is not necessary to practice the present invention. Nonetheless, it is contemplated that, since p53 mutations are rare in CTCL and a major downstream effector p21 is not silenced, methylation-dependent silencing of BRCA1 plays a role in abrogation of the p53-dependent response in these tumors.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method comprising:
a) providing a plasma sample from a subject, said plasma sample comprising genomic DNA, wherein said genomic DNA comprises a plurality of promoters from different genes;
b) isolating and digesting said genomic DNA with a methylation sensitive restriction enzyme under conditions such that unmethylated CpG islands in said promoters are cleaved while methylated CpG islands in said promoters are not cleaved;
c) contacting said digested genomic DNA with gene specific primers, wherein said gene specific primers are configured to hybridize to said genomic DNA and amplify different promoters from different genes including DAPK, FAS, MCT1, p16, PAX5, THBS, TRANCE, and VHL, and wherein said contacting is under conditions such that fragments of said plurality of promoters comprising uncleaved CpG islands are amplified, while cleaved promoters comprising cleaved CpG islands are not amplified; and
d) detecting the presence or absence of DNA methylation in each of said plurality of promoters based on the amplification, or lack of amplification, of said fragments to generate a methylation profile for said subject.

2. The method of claim 1, wherein said method further comprises comparing said methylation profile to one or more standard methylation profiles, wherein said standard methylation profiles are selected from the group consisting of methylation profiles of non-cancerous samples and methylation profiles of cancerous samples.

3. The method of claim 1, wherein said methylation-sensitive restriction enzyme comprises Hin6I.

4. The method of claim 1, further comprising the step of i) separating said plasma sample into a control sample and an experimental sample, and ii) adding control nucleic acid to both said control and experimental samples, wherein said control nucleic acid comprises at least one known CpG island that is unmethylated.

5. The method of claim 4, wherein said control sample is not exposed to said digesting and said experimental sample is exposed to said digesting, and wherein both said control and experimental samples are contacted with primers specific for said control nucleic acid under conditions such that a fragment of said control nucleic acid is amplified only if said known CpG island is uncleaved.

6. The method of claim 5, further comprising comparing any fragments amplified in said control and experimental samples to confirm that said digesting in step b) is complete.

7. The method of claim 2, wherein said digesting is performed to completion.

* * * * *

UNITED STATES PATENT AND TRADEMARK OFFICE
CERTIFICATE OF CORRECTION

| | | |
|---|---|---|
| PATENT NO. | : 7,666,589 B2 | Page 1 of 1 |
| APPLICATION NO. | : 10/677701 | |
| DATED | : February 23, 2010 | |
| INVENTOR(S) | : Victor V. Levenson et al. | |

It is certified that error appears in the above-identified patent and that said Letters Patent is hereby corrected as shown below:

Col. 1, line 9:

Delete "may have certain rights" and substitute therefor "has certain rights"

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,666,589 B2
APPLICATION NO. : 10/677701
DATED : February 23, 2010
INVENTOR(S) : Levenson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 308 days.

Signed and Sealed this

Seventh Day of December, 2010

David J. Kappos
*Director of the United States Patent and Trademark Office*

UNITED STATES PATENT AND TRADEMARK OFFICE
CERTIFICATE OF CORRECTION

PATENT NO. : 7,666,589 B2
APPLICATION NO. : 10/677701
DATED : February 23, 2010
INVENTOR(S) : Victor V. Levenson et al.

It is certified that error appears in the above-identified patent and that said Letters Patent is hereby corrected as shown below:

Col. 1, lines 7-8:

Delete "application was funded in part by grant number R21 CA097511 awarded by the National Cancer Institute" and substitute therefor "invention was made with government support under 1 R21 CA097511 awarded by National Institutes of Health".

Signed and Sealed this
Thirteenth Day of March, 2012

David J. Kappos
*Director of the United States Patent and Trademark Office*